United States Patent [19]

Shichman et al.

[11] Patent Number: 5,425,489

[45] Date of Patent: Jun. 20, 1995

[54] FASCIA CLIP AND INSTRUMENT

[75] Inventors: Daniel Shichman, Trumbull; Turi Josefsen, Westport, both of Conn.; Boris Zvenyatsky, Bronx, N.Y.

[73] Assignee: United States Surgical Corporation, Norwalk, Conn.

[21] Appl. No.: 194,139

[22] Filed: Feb. 9, 1994

Related U.S. Application Data

[63] Continuation of Ser. No. 73,632, Jun. 8, 1993, abandoned, which is a continuation of Ser. No. 686,795, Apr. 17, 1991, abandoned, which is a continuation-in-part of Ser. No. 631,373, Dec. 20, 1990, abandoned.

[51] Int. Cl.⁶ .................. A61B 17/04; B25C 5/02
[52] U.S. Cl. ........................ 227/108; 227/19; 227/175; 606/220
[58] Field of Search ........... 606/142, 143, 151, 220; 227/19, 108, 175, 176

[56] References Cited

U.S. PATENT DOCUMENTS

| | | | |
|---|---|---|---|
| 2,182,594 | 12/1939 | Matveyeff | 227/108 |
| 2,234,808 | 3/1941 | Schafroth | 227/108 |
| 2,277,139 | 3/1942 | Niemand | 227/19 |
| 2,578,212 | 12/1951 | Warren | . |
| 2,707,783 | 5/1955 | Sullivan | . |
| 2,770,804 | 11/1956 | Schafroth | 227/108 |
| 3,646,801 | 3/1972 | Caroli | 227/19 |
| 3,775,825 | 12/1973 | Wood et al. | 606/143 |
| 4,162,678 | 7/1979 | Fedotor et al. | 227/19 |
| 4,448,193 | 5/1984 | Ivanov | 606/143 |
| 4,493,322 | 1/1985 | Becht | 227/19 |
| 5,067,958 | 11/1991 | Sandhaus | 606/142 |

FOREIGN PATENT DOCUMENTS

| | | |
|---|---|---|
| 0419071 | 3/1991 | European Pat. Off. . |
| 2335192 | 12/1976 | France . |
| 425857 | 10/1948 | Italy ................. 24/712.5 |

Primary Examiner—Gary Jackson

[57] ABSTRACT

An apparatus for applying a surgical clip which comprises a staple having a central portion and first and second legs extending from said central portion. A retainer is provided having an opening dimensioned for passage of an end portion of each of said legs when the legs are bent from an open position to a closed position. The apparatus comprises staple forming means in the form of a pair of pivotable members movable from an open position to a closed position when slid into engagement with a camming surface. Staple pusher means engage the central portion of the staple and slides the staple distally into contact with an anvil and with the pivotable members to bend the staple legs to their closed position.

20 Claims, 6 Drawing Sheets

FASCIA CLIP AND INSTRUMENT

This is a continuation of application Ser. No. 08/073,632, filed on Jun. 8, 1993 which is a continuation of application Ser. No. 07/686,795, filed on Apr. 17, 1991, now abandoned, which is a continuation in part of application Ser. No. 07/631,373, filed on Dec. 20, 1990, now abandoned.

BACKGROUND OF THE INVENTION

1. Field of the Invention

This invention relates to a surgical clip for closing an incision in body tissue and more particularly to a fascia clip of two piece construction comprising a staple and a retainer and an instrument for applying the staple.

2. Description of the Related Art

Surgical fasteners have been used in surgical procedures to eliminate the need for suturing, which is both time consuming and inconvenient. In these applications the surgeon can use a fastener implanting device loaded with one or more surgical fasteners to accomplish in a few seconds what would have taken many minutes to perform by suturing. This reduction in operating time reduces blood loss and trauma to the patient.

In some applications, two part surgical fasteners are used in which the fastener is inserted at the wound site and is engaged by a retainer to hold the fastener in place. These retainers prevent the fastener from working loose from the tissue. Since the two piece fasteners cannot easily be unlocked and are not easily removable, they are made of bioabsorbable material.

Possible materials for such two part fasteners include polymers and copolymers of glycolic acid (i.e. hydroxyacetic acid), the cyclic dimer of glycolic acid ("glycolide"), lactic acid, the cyclic dimer of lactic acid ("lactide") and related monomers. Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459–1464 (1979), and D. F. Williams (ed.) Biocompatibility of Clinical Implant Materials, Vol. II, ch. 9: "*Biodegradable Polymers*" (1981).

The use of prior fasteners and instruments has not been entirely suitable for all types of tissue. For example, many of the prior fasteners are not suitable for closing fascia tissue incisions because the tissue is relatively thick and not easily manipulated. U.S. Pat. No. 4,950,284 discloses one type of clip suitable for fascia tissue. The clip comprises a longitudinal strap which extends through an opening in the proximal end of the base and emerges through an opening at the distal end of the base.

The need exists for an improved surgical clip which can be utilized for fascia tissue, and is easy to manufacture, easy to manipulate, can be applied with accuracy, and provides a secure closure of the incision. The need also exists for an instrument for applying such surgical clip.

SUMMARY OF THE INVENTION

The present invention provides an improved surgical fascia clip for closing incisions in body tissue. The fascia clip comprises a retainer and a flexible staple having a pair of legs extending from the central portion. The legs of the staple are movable from an open position in which the legs are spaced apart and extend substantially parallel or obliquely to one another to a closed position where the legs are bent inwardly toward each other so that the end portions of the legs extend substantially parallel to the central portion of the staple and extend through an opening in the retainer. The legs may include a plurality of teeth which are engaged by a pawl disposed within the retainer to thereby improve securement of the legs within the retainer. Both the staple and the retainer are preferably and advantageously made from a bioabsorbable material.

The present invention also provides an instrument for applying the staple. The instrument comprises staple forming means for bending the staple legs inwardly towards each other and staple pusher means for engaging the central portion of the staple and advancing it distally. The staple forming means may comprise a pair of pivotable members which pivot from an open position to a closed position by engagement with a camming surface. The staple pusher means moves the staple legs into contact with an anvil and with the closed pivotal members. The pivotable members are preferably spring biased in the open position. Spring means engageable with the staple pusher means may also be provided to prevent distal movement until the staple forming means has advanced a desired distance.

BRIEF DESCRIPTION OF THE DRAWINGS

The present invention will be more fully appreciated as the same becomes better understood from the following detailed description of the present invention when considered in connection with the accompanying drawings in which:

FIG. 2b is an enlarged side view of the distal end portion of one of the legs of the staple of FIG. 2a;

DETAILED DESCRIPTION OF THE PREFERRED EMBODIMENTS

Figure 1:
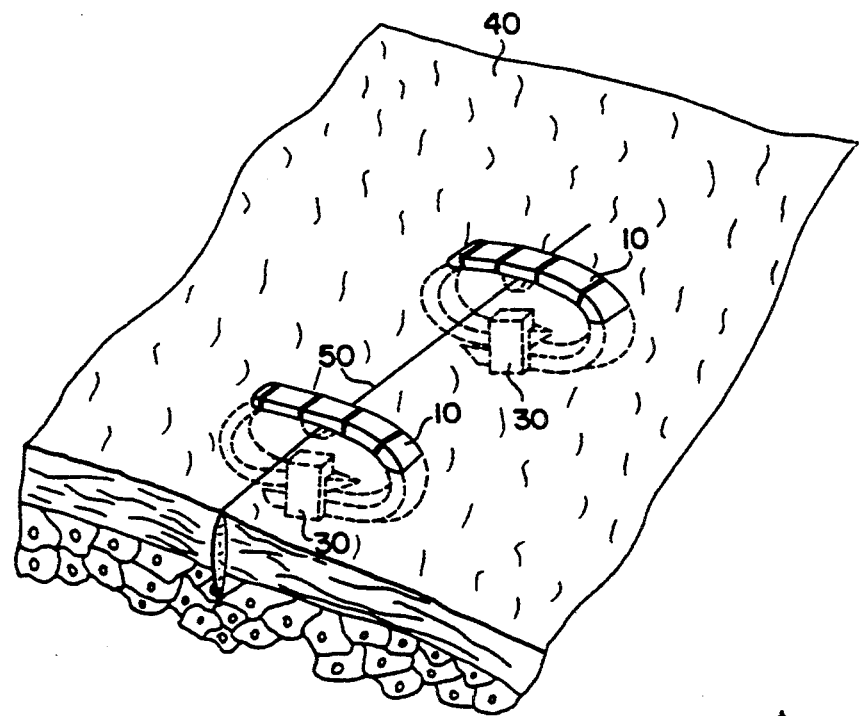
FIG. 1 illustrates a perspective view of a plurality of surgical clips of the present invention shown closing an incision in body tissue.

With reference now to the drawings, wherein like reference numerals represent identical parts throughout the several views, and more particularly to FIG. 1, a plurality of surgical clips of the present invention are shown closing an incision 50 in a layer of body tissue 40. The clips can advantageously be used to close an incision or wound in various types of tissue, including fascia tissue which is relatively thick and not easily manipulated. As illustrated, each surgical clip is of a two piece construction comprising a fastener or staple 10 and a retainer 30.

As will be described in more detail below, staple 10 is sufficiently flexible so that it can be bent by an appropriate instrument from an open position where the legs are spaced apart (see e.g. FIG. 2A) to a closed position where the legs are bent inwardly towards one another and extend in a direction parallel to the longitudinal axis of the central portion (see e.g. FIG. 5), thereby forming an elongated oval-shaped configuration. In the closed position as shown, the end portion of the staple legs extend through an opening in the retainer 30; the retainer thereby functions to help maintain the legs in their closed position.

Figure 2B:
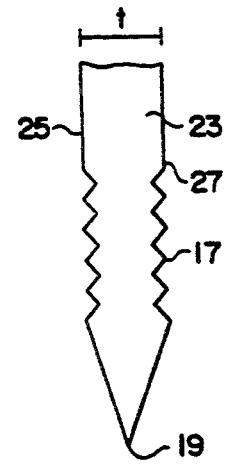
Figure 2A:
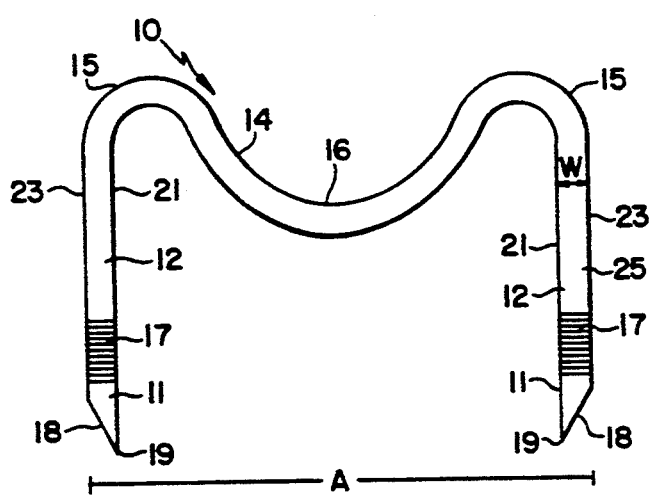
FIG. 2a illustrates a front view of the staple of the surgical clip of the present invention shown in an open position.

Referring more particularly to FIG. 2A, the staple 10 has a central portion 14 and a pair of legs 12 extending downwardly therefrom. The legs 14 are disposed substantially parallel to one another and substantially perpendicular to central portion 14. An indentation 16 is formed in central portion 14 to facilitate insertion of the staple 10 and to allow a tighter grip on the tissue held within the confined area, i.e. the oval shaped area, of the closed staple 10. Curved portions 15 are formed at the juncture of central portion 14 and legs 12 to allow bending of legs 12 to their closed position. The distal tip portion 11 of each staple leg 12 has an inclined outer surface 18 terminating in a sharp pointed tip 19 which facilitates penetration of the staple 10 into the tissue. Reference numeral 25 designates the front surface of the legs 12 and reference numerals 21 and 23 designate the inner side surface and outer side surface of the legs 12, respectively.

To improve retention of fastener legs 12 within retainer 30, a ratchet mechanism is provided in the form of a pawl disposed within the retainer adapted to engage one of the teeth formed on the staple legs. The plurality of teeth also permit the clip to automatically adjust to varying thickness of tissue. More particularly, a plurality of teeth 17 are provided at the end portion of legs 12, preferably slightly proximally of distal tip portion 11. As shown in FIG. 2B, the teeth 17 are formed in both the front and rear surfaces 25 and 27, respectively, of each leg 12 to engage opposing pawls of retainer 30 which will be described below. Although each fastener leg 12 is shown with five teeth on opposing surfaces, clearly a fewer or larger number of teeth or teeth on only one side of the leg could be provided so long as they achieve their securement and/or adjustment function. Additionally, other means can be provided to enhance securement of staple legs 12 within retainer 30 such as an interlocking mechanism.

Figure 6A:
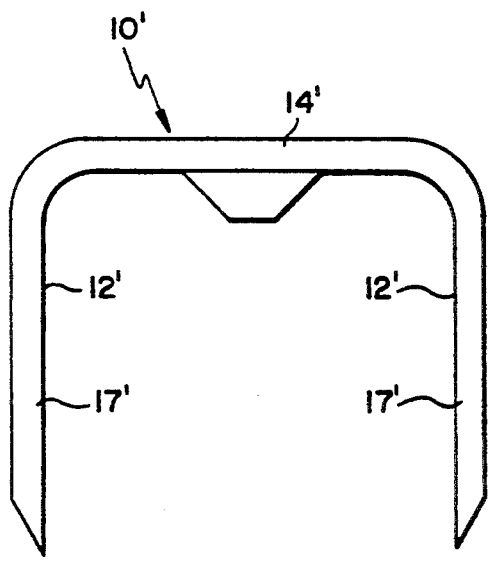
FIG. 6A illustrates a front view of an alternate embodiment of the staple of the surgical clip of the present invention.

In an alternate embodiment shown in FIG. 6A, staple 10' includes a pair of legs 12' extending substantially perpendicularly from central portion 14'. A plurality of teeth 17' are also provided. Unlike the staple 10 of FIG. 2a, the staple legs 12' are joined by a substantially linear central portion 14. That is, there is no indentation formed in the central portion 14.

Figure 6B:
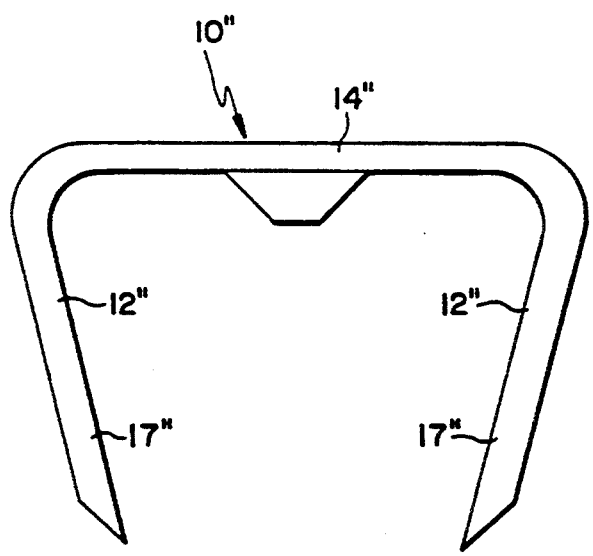
FIG. 6B illustrates a front view of another alternate embodiment of the staple of the surgical clip of the present invention.

In another alternate embodiment of the staple of the present invention shown in FIG. 6B, the staple 10" includes a pair of legs 12" extending obliquely from central portion 14". The legs are bent inwardly as in the aforementioned embodiments to engage a centrally positioned retainer. A plurality of teeth 17" are also provided proximally of the distal tip. Staple 10" can optionally include an indentation as in staple 10 of FIG. 2A.

Referring back to FIG. 2A, staple 10 has a width w, measured as the distance between side surfaces 21 and 23, which is preferably substantially uniform throughout its length, with the exception of tapered distal tip portion 11 which is of reduced width. The thickness t of the staple legs 12 (FIG. 2B) and of the central portion 14, measured as the distance between front surface 25 and rear surface 27, is also preferably substantially uniform and is preferably greater than width w. Clearly, the width and thickness can vary at different parts of the staple. For example, the central portion can be formed with a thickness greater than that of the legs or vice versa. Alternately, the staple legs and/or central portion can be formed of square cross section so that its width is equal to its thickness or can be formed so that its width exceeds its thickness.

In one embodiment, the length A (FIG. 2A) measured as the distance between the side surfaces 23 of opposing staple legs 12 in the open position, is approximately 1.480 inches and the length B (FIG. 5), measured as the distance between the side surfaces 21 of opposing staple legs 12 in the closed position is approximately 0.921 inches. Clearly, these dimensions provide only an example of one of the numerous sizes in which the staples can be formed. The size of the staple as well as the ratios of width and thickness of various parts can vary depending on its particular use.

The staple 10 is preferably composed of a material which is sufficiently flexible to bend without breaking and is strong enough to provide a firm grip on the body tissue to allow healing of the incision. It is preferably composed of a bioabsorbable material such as homopolymers or copolymers of lactide, glycolide, polydioxanome, trimethyl carbonate, polythylene oxide or other bioabsorbable polymer materials or blends of these respective copolymers. One preferred material is made of a copolymer of lactide and glycolide made from approximately 18% m glycolide and 82% m lactide. Another possible bioabsorbable material for constructing the staple is disclosed in U.S. Pat. No. 4,523,591 to Kaplan et al, and U.S. Pat. No. 4,744,365 to Kaplan et al, herein incorporated by reference. Clearly, the materials disclosed in the patents and literature listed in the Background section of this application can also be utilized.

Figure 5:
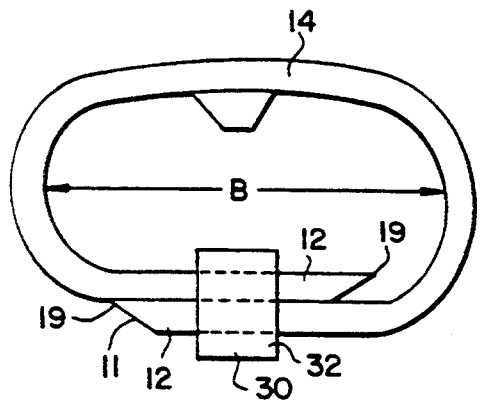
FIG. 5 illustrates a front view of the staple and retainer of the present invention showing the staple in the closed position.

Turning now to the retainer 30 of the surgical clip of the present invention, as shown in FIG. 5, the retainer 30 is positioned midway between opposing staple legs 12 and is spaced apart a sufficient distance from the central portion of staple 10 to receive the distal tip portion 11 of legs 12 when bent to the closed position.

Figure 3:
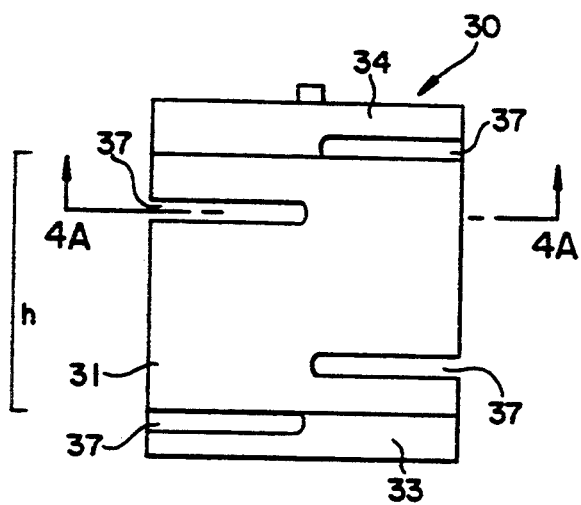
FIG. 3 illustrates a front view of the retainer of the surgical clip of the present invention.
Figure 4B:
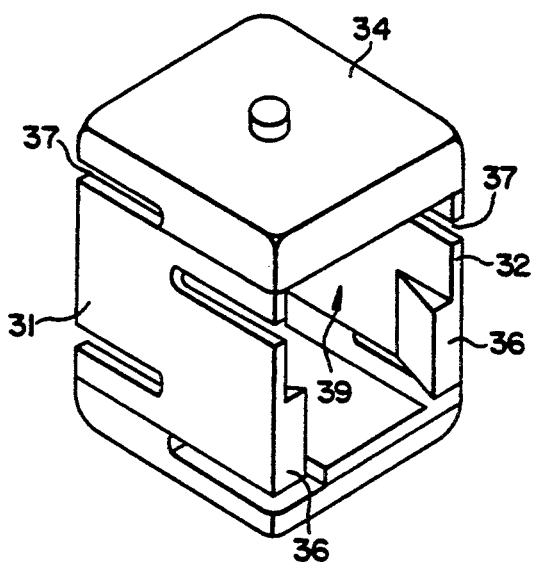
FIG. 4b illustrates a side perspective view of the retainer of the surgical clip.
Figure 4A:
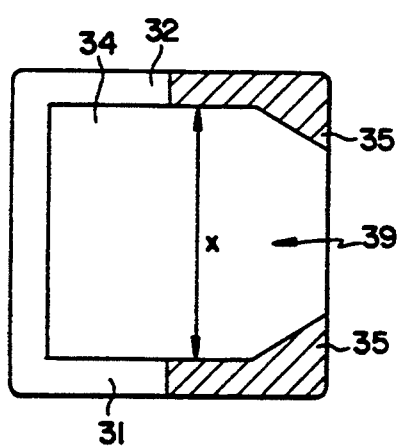
FIG. 4a is a cross-sectional view of the retainer taken along lines 4a—4a of FIG. 3.

The retainer 30, as shown in FIG. 3, has top and bottom portions 34, 33, and front and rear walls 31, 32 (FIG. 4A) positioned between the top and bottom portions. As shown, a longitudinal slot 37 is formed in both the bottom and top portions 33, 34 and two longitudinal slots 37 are formed in the front wall 31 of the retainer 30. Similarly, two corresponding longitudinal slots are formed in rear wall 32 and in the rear surface of the bottom and top portions 33, 34. These slots maintain the resiliency of retainer 30 for the reasons explained below. The slots are illustratively shown starting at the edge of the front (or rear) wall and terminating at a midline of the retainer 30. However, clearly the slots which are preferably formed when the retainer is molded, can be formed of other configurations and in different locations and a fewer or larger number of slots can be provided.

The retainer 30 has a hollow portion forming an opening or passageway 39 extending through its entire length which is dimensioned to receive a portion of both staple legs 12. The passageway 39 is formed between top and bottom portions 34, 33 and bounded by front and rear walls 31, 32 respectively.

Protruding from the inside surface of an upper portion of both walls 31, 32 is an inwardly extending projection or pawl 35 (See FIG. 4A) which is adapted to engage the teeth, 17 of one of the staple legs 12. Similarly, a pawl, designated by reference numeral 36 in FIG. 4B, protrudes from an inside surface of lower portion of front and rear walls 31, 32 to engage opposing teeth 17 of the other staple leg 12. The passageway 39 is preferably dimensioned to have a height h, measured as the distance between top portion 34 and bottom portion 33 (see FIG. 3), slightly less than the combined thickness t of the legs 12 and has a width x, measured as the distance between front wall 31 and rear wall 32 (FIG. 4a), slightly less than the width w of each staple leg 12. These dimensions advantageously result in the resilient retainer walls being slightly expanded when the legs 12 are inserted through passageway 39 and then springing back due to their resiliency to more tightly grasp the legs. Clearly, the relationship of the dimensions of the passageway 39 and the staple legs 12 will vary depending on the configuration of the legs in the closed position as will become apparent from the discussion below.

The retainer is preferably made of a copolymer of lactide and glycolide made from approximately 18% m glycolide and 82% m lactide. Other possible bioabsorbable materials include those discussed above with respect to the staple 10.

Turning now to the closed configuration of staple 10, and more particularly to FIG. 5, legs 12 are bent into their closed position so that they extend through passageway 39 of retainer 30. As illustrated, retainer 30 is positioned distally of central portion 14 and centered with respect thereto. Each staple leg 12 enters through one side of passageway 39, extends through the entire length of the passageway, and emerges from the opposite side. Thus, a distal portion of each leg 12 extends beyond the edges of front and rear walls 31, 32. In an alternate embodiment shown in FIG. 7, the legs 12 extend into, but not beyond, the passageway 39 of retainer 30 so that the distal end portions of legs 12 terminate within retainer 30. The central portion 14 in both embodiments is substantially linear in the closed position as movement of staple legs 12 straighten central portion 14 to thereby remove the indentation 16.

Figure 7:
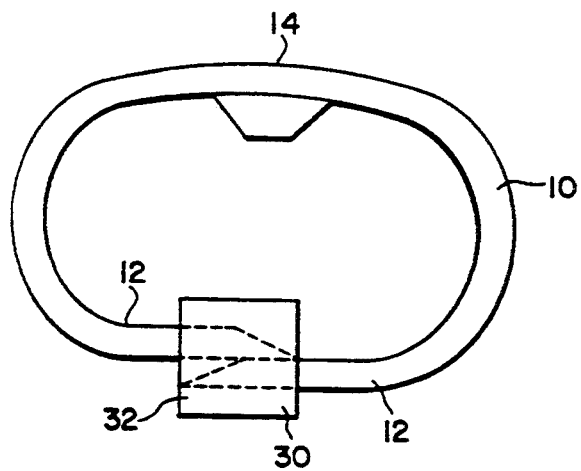
FIG. 7 illustrates a front view of an alternate embodiment of the staple and retainer of the present invention showing the staple in the closed position.

In the embodiment shown in FIGS. 5 and 7, the closed staple legs 12 are positioned one atop the other and in abutting relationship. However, alternatively, the legs can be spaced apart from one another in the closed position. In such configuration, a separate passageway can optionally be provided for each staple leg. In another alternate embodiment, the staple legs can be arranged in side-by-side relationship within the passageway rather than above one another. The retainer and passageway would be appropriately dimensioned to accommodate this configuration.

Figure 8:
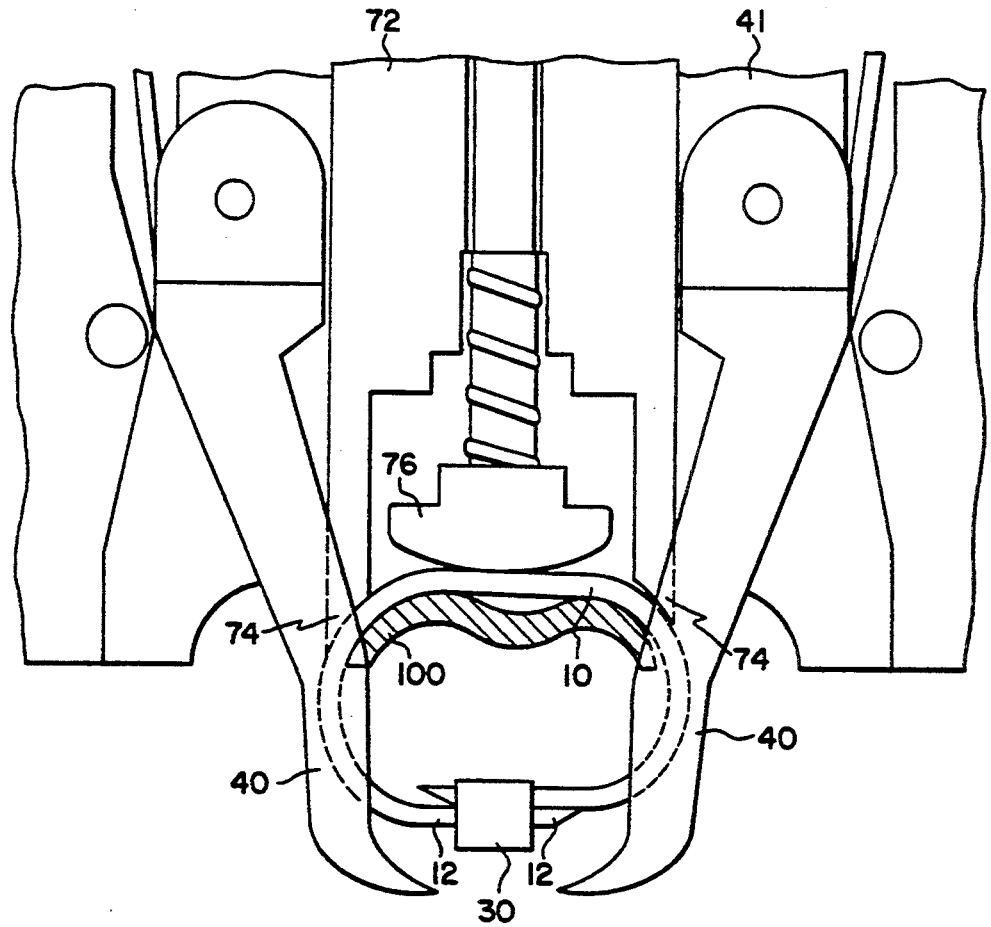
FIG. 8 illustrates an enlarged view of a portion of the apparatus for applying the surgical clip of the present invention.

FIG. 8 illustrates generally some of the components of an apparatus which can be utilized to apply the surgical clip of the present invention to body tissue. The components include a pair of approximators or arms 40 mounted on a base 41 and configured to both grasp the body tissue and to bend the staple legs 12, a staple pusher 72 having spaced apart fingers 74 to engage and push staple 10 distally, an anvil 100, and an alignment member 76 to engage the central portion or indentation of the staple 10 to facilitate centering of the staple. An actuator assembly for operating these components (not shown in FIG. 8) activates both base 41 which supports approximators 40 and staple pusher 72 in a manner described below.

Figure 9:
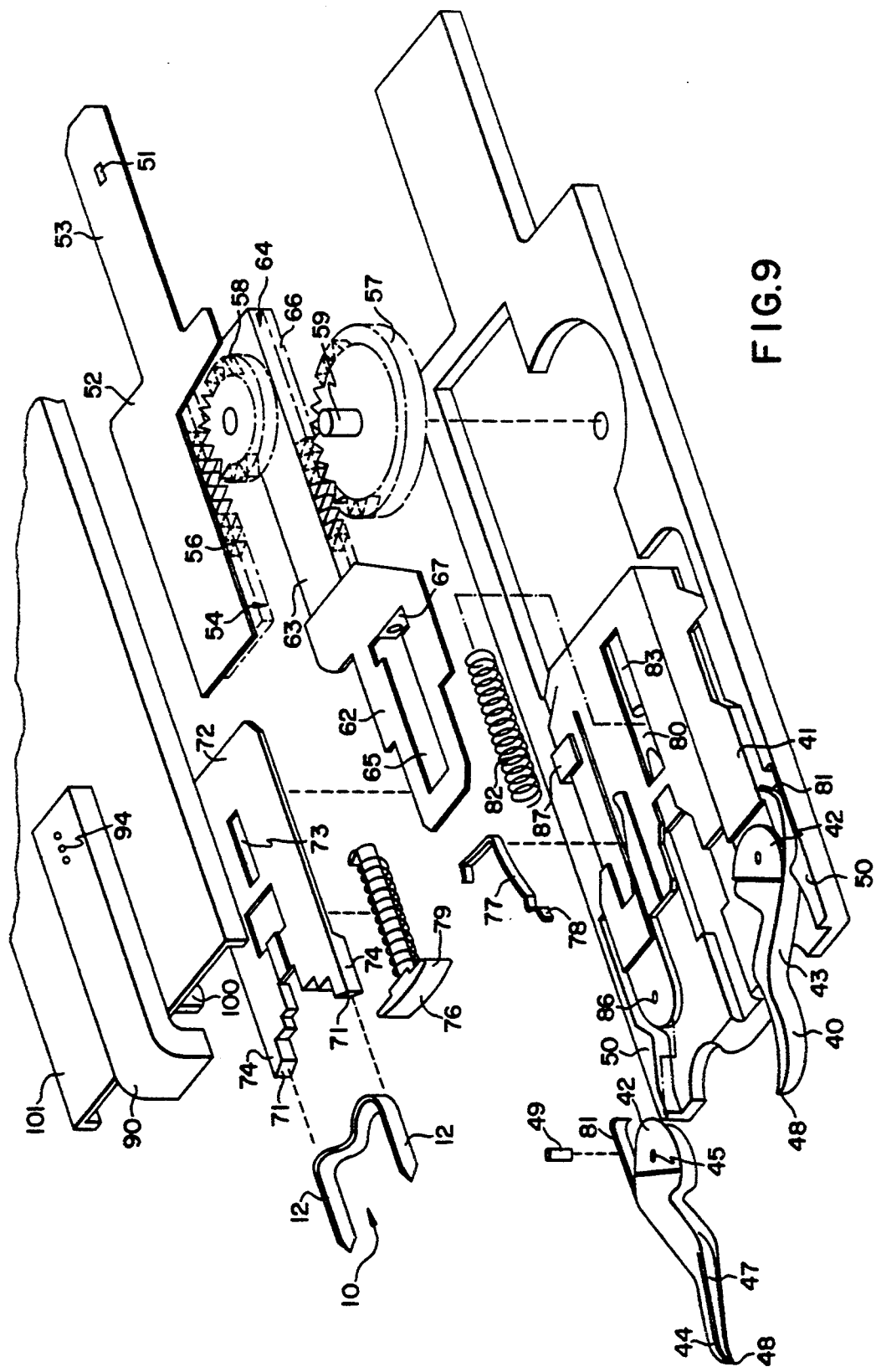
FIG. 9 is an exploded view of the apparatus for applying the staple of the present invention.

Turning more specifically to FIG. 9, the actuator assembly comprises a proximal actuator 52 and a distal actuator 62, each slidably mounted within a housing (not shown) and each engageable with a gear of the gear assembly which functions as a stroke multiplier as is known in the art. The actuator assembly is activated by a suitable trigger mechanism (not shown). Actuator 52 has a proximal extension 53 which includes an aperture 51 formed therein for mounting to the apparatus housing and allows for sliding movement. Actuator 52 further includes a rack 54 located at the distal portion which has a plurality of longitudinally aligned teeth 56 adapted to engage small gear 58 of the gear assembly. Though rack 54 is shown as integral with actuator 52, alternatively the rack can be a separate component secured to the actuator. Small gear 58 is mounted on a support pin 59.

Distal actuator 62 has a proximal portion 63 having an integral rack 64 containing longitudinally disposed teeth 66. As with rack 54 of actuator 52, alternatively, rack 64 can be a separate component connected to actuator 62. Teeth 66 of rack 64 are adapted to mesh with large gear 57 which is also mounted to support pin 59 so that gears 57 and 58 can simultaneously rotate. An elongated longitudinally extending slot 65 is formed in the distal portion of actuator 62 to receive a return spring for biasing distal actuator 62 proximally. A projection 67, having spaced apart legs, extends from the rearmost edge of slot 65 and when assembled straddles a rod 83 of base 41. Actuator 62 is connected to the base 41 so that movement of actuator 62 moves base 41 in the same direction.

Base 41 has an elongated longitudinal slot 80 configured to receive a return spring 82 which is mounted on rod 83 and biases base 41 proximally so that base 41 returns to its proximal (open) position after the staple 10 is formed. Rod 83 receives spaced apart legs of projection 67 of distal actuator 62 so that base 41 will be carried by actuator 62. A protruding member 87 is formed on a side edge of base 41.

Turning now to the pair of approximators or pivotable arms 40 for forming (bending) the staple, each approximator 40 includes a widened head portion 42, a concave or inclined outer surface 43, and an end portion 44 having a sharpened pointed tip 48 to pierce the tissue. The approximators 40 are pivotally mounted to a distal end of base 41 by a pin 49 inserted through aligned holes 45 and 86 of the head portion 42 and base 41, respectively. Each approximator 40 is biased in the open position by a leaf spring 81 and is pivotable between a normal open position where the approximators are the furthest distance apart and a closed position where the approximators are positioned closer together to receive the staple legs 12 to force them into their bent position. Each approximator 40 has a channel 47 formed between its upper and lower walls to receive the staple leg 12 to better control bending of the leg.

With continued reference to FIG. 9, formed in the housing are a pair of oppositely disposed stationary camming surfaces 50 which function to pivot the approximators 40 into their closed position. As approximators 40 slide forwardly (distally) along with base 41, angled outer surface 43 engages the angled inwardly protruding surface of camming surface 50 which is configured and dimensioned to force the approximators 40 to pivot on pin 49 inwardly towards one another into their closed position. This pivotal movement of approximators 40 is more clearly shown in FIGS. 10–12.

Figure 12:
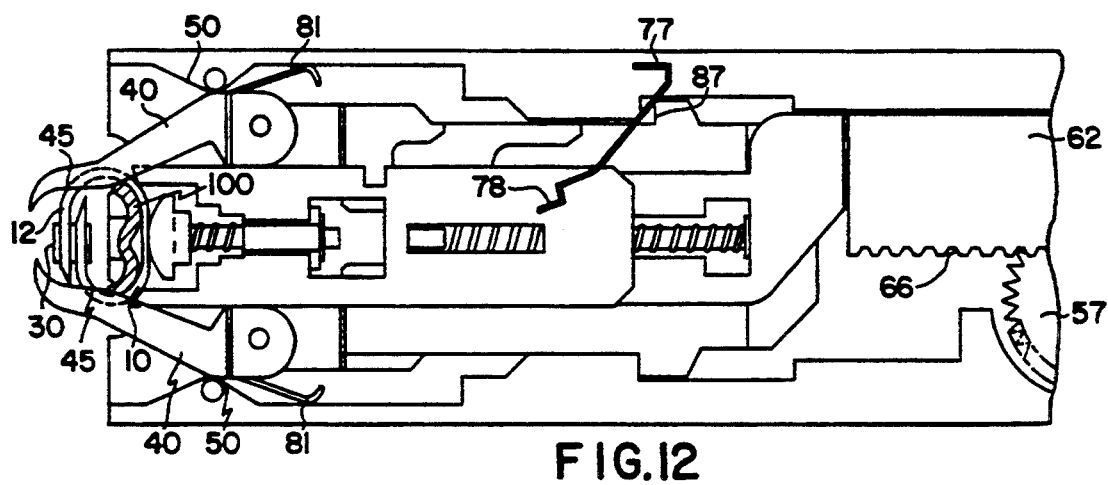
FIG. 12 is a plan view of the front portion of the assembled apparatus in its fired position.

Turning now to the staple pusher 72 for moving the staple 10 distally into engagement with approximator 40, staple pusher 72 is mounted to distal actuator 62 so slot 73 overlies slot 65 and is slidable between a proximal position (FIG. 10) and a distal position (FIG. 12). Staple pusher 72, as shown in FIG. 9, has spaced apart fingers 74 at its distal end with end surfaces 71 substantially conforming to the curved shape of the central portion 14 of staple 12 to facilitate movement of the staple. Staple pusher 72 also includes a spring mounted alignment member 76 which is positioned between the pusher fingers 74. Alignment member 76 has a transversely extending shoulder 79 providing a staple engaging surface to assist in alignment and centering of staple during application.

A slot 75 (FIG. 10) is formed in the edge of staple pusher 72 to receive end 78 of a spring 77. Spring 77 is biased into slot 75 and functions to prevent distal movement of staple pusher 72 when engaged in the slot. When edge 78 of spring 77 is disengaged from slot 75 in the manner described below, the staple pusher 72 is released and distal movement is allowed.

A wrap 101 is positioned above the approximators 40 and has a downwardly extending anvil 100 which is centered with respect to staple pusher 72. The staple legs 12 are bent inwardly when pusher fingers 74 of staple pusher 72 push staple 10 distally into contact with anvil 100. The radius of curvature of anvil section 106 differs from the radius of curvature of anvil section 108 (See FIG. 10) to cause the staple legs 12 to bend into the closed configuration shown in FIG. 5 where one of the legs 12 is positioned above the other leg. A spring mechanism is provided on wrap 100 to allow withdrawal of anvil 100 after application of staple 10.

A curved retainer channel member 90, illustrated in FIG. 9, is mounted to wrap 101 above the stapler pusher 72 and approximators 40 and functions to release a retainer 30 into the appropriate position to receive the staple legs 12. A series of apertures 94 are formed at a proximal end of channel member 90 to to receive fastening members for mounting to wrap 101 (not shown).

The operation of the aforementioned components of the apparatus will now be described. The approximators 40, distal actuator 62 and staple pusher 72 are in the initial pre-fired position shown in FIG. 10. (Proximal actuator 52 (not shown) is also in the proximal position.) Spring 77 is positioned in slot 75 as shown to prevent distal movement of the staple pusher 72. The approximators 40 are biased in their normal open position by spring 81.

Figure 10:
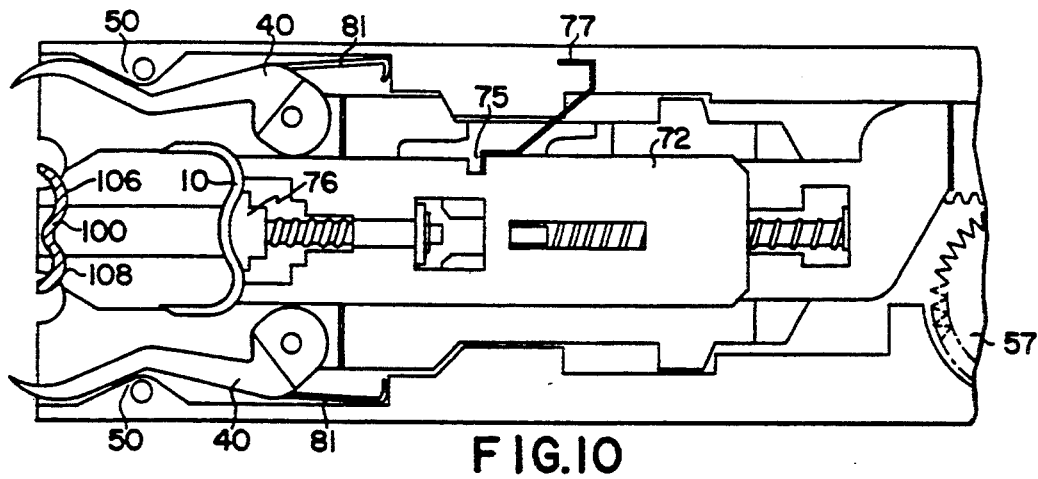
FIG. 10 is a plan view of the front portion of the assembled apparatus of FIG. 9 in its pre-fired position.
Figure 11:
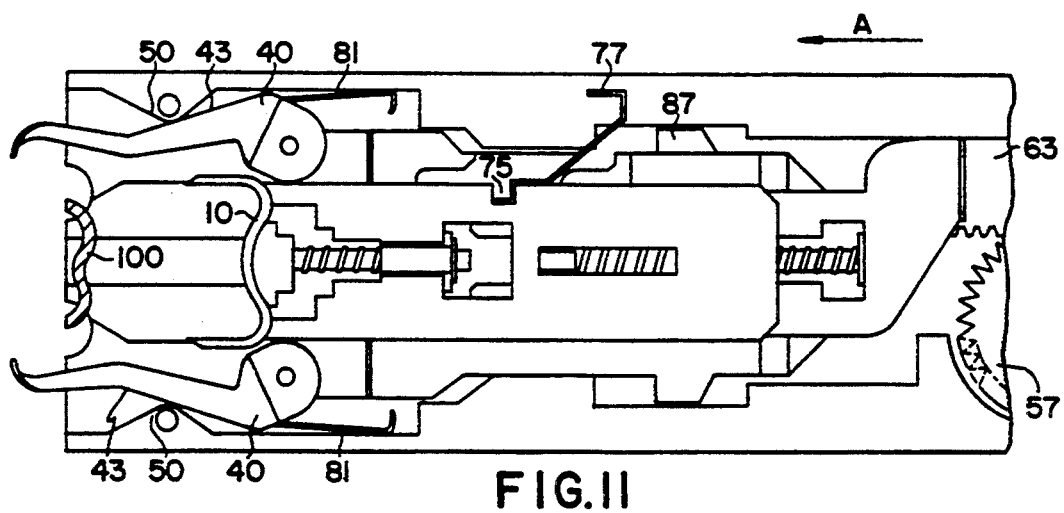
FIG. 11 is a plan view of the front portion of the assembled apparatus in its intermediate position.

Upon actuation of the apparatus, proximal actuator 52 is slid distally (forwardly) in the direction of arrow A so that teeth 56 of rack 54 rotate small gear 58 counterclockwise. Such rotation of small gear 58 causes rotation of large gear 57 in the same direction, thereby activating distal actuator 62 as the gear teeth engage teeth 66 of rack 64. As actuator 62 is slid distally by large gear 57, it carries mounted base 41 (and attached approximators 40) in the same direction. As base 41 moves distally, the outer surface 43 of approximators 40 engage camming surfaces 50 which overcome the bias of spring 81 and force the approximators 40 to begin pivoting inwardly towards each other. FIG. 11 illustrates the approximators 40 in this intermediate position. Note that staple pusher 72 remains in the same retracted position as shown in FIG. 10 due to the positioning of spring 77 within slot 75.

Continued distal movement of actuators 52, 62 translates to further distal movement of base 41 to further cam approximators 40 towards their closed position. Sufficient forward movement of base 41 results in protruding surface 87 of base 41 contacting spring 77 to force it out of slot 75 and slide it out of engagement with staple pusher 72 (see FIG. 12). This releases staple pusher 72 so that further movement of base 41 now causes pusher 72 to slide forwardly which in turn pushes staple 10 forwardly so that staple legs 12 contact and are formed around anvil 100. Staple legs 12 are further received in the channel 47 of closed approximators 40 and are bent inwardly into retainer 30. FIG. 12 shows the apparatus in this fired position where staple 10 has been formed and engages retainer 30.

After formation of staple 12, actuators 52 and 62 are moved proximally (rearwardly) to thereby retract staple pusher 72 and base 41 to their proximal positions. Proximal movement of base 41 opens approximators 40 as they disengage from camming surfaces 50. Spring 77 returns to slot 75 and once again engages staple pusher 72. Thus, the apparatus returns to its original pre-fired position shown in FIG. 10.

In use, to close an incision in fascia tissue, the pivotally mounted approximators 40 are each placed on an opposing side of the incision and inserted into the tissue. Such placement of the approximators 40 likewise results in the centering of the staple 10 above the incision. The approximators 40 are then pivoted inwardly as described above, thereby pulling the two tissue portions on opposing sides of the incision towards each other. Retainer 30 is guided by any suitable means, such as the curved channel member 90 shown in FIG. 9, to a distal position underneath the incision (below the top surface of the tissue) and transversely centered with respect to the incision. The pusher 72 is actuated in the manner described above and moves forwardly so that the staple engaging fingers 74 press against the juncture between the central portion 14 and legs 12 (adjacent curved portion 15) to move staple 10 distally. Distal movement of staple 10 results in engagement with the anvil 100 and with channel 47 formed in the inner side wall of approximators 40 which force the staple legs 12 inwardly toward one another. Continued distal movement causes further inward bending of the legs 12 which allows them to pass through opposite sides of the passageway 39 of retainer 30. When inward bending is complete i.e. the staple is forced to its closed position, the appropriate tooth 17 located at the distal end portion of the legs 12 is engaged and secured by the pawl of the retainer 30 to thereby help prevent withdrawal of the legs from the retainer passageway 39. As a result, the staple 12 and retainer 30 form a substantially continuous, e.g. oval, enclosure around the incision, thereby ensuring a firm grip on the fascia tissue and a secure closure around the incision. After the clip is applied, the staple pusher 72 is retracted as described above and the approximators 40 are rotated outwardly and removed from the tissue leaving the clip firmly in place. As shown in FIG. 1, a plurality of clips can be inserted along the length of the incision by moving the apparatus to a new position along the incision and applying a new clip in the manner described above.

It will be understood that the foregoing is illustrative of the principles of the invention and that various modifications can be made by those skilled in the art without departing from the scope and spirit of the present invention.

What is claimed is:

1. In combination: a staple having a pair of legs; a retainer having an opening and adapted to receive said staple legs; and a surgical apparatus for applying said staple to said retainer, said apparatus containing said staple and said retainer therein, said apparatus comprising first and second pivotable arms, means for moving said staple distally towards said retainer, and means for pivoting said arms between an open position and a closed position, so the staple legs contact said arms in said closed position and are thereby bent at an angle to extend inwardly towards each other and enter the opening in the retainer.

2. A surgical apparatus as recited in claim 1, wherein said pivot means is a pair of opposing stationary camming surfaces for pivoting said arms to the closed position, and the apparatus further comprises means for sliding said arms istally to engage said camming surfaces.

3. A surgical apparatus as recited in claim 1, further comprising an alignment member connected to said staple pusher means to engage the staple.

4. A surgical apparatus as recited in claim 1, wherein each said arm has a widened head portion at its proximal end and a narrowed distal portion having a pointed tip, each said head portion mounted to the apparatus by a pin.

5. A surgical apparatus as recited in claim 1, further comprising a spring member movable from an engaged position to a disengaged position to thereby release said staple moving means.

6. A surgical apparatus for applying a surgical staple which has a central portion and a pair of spaced apart legs extending from the central portion, said apparatus comprising:

a housing having proximal and distal end portions and oppositally disposed raised stationary cam surfaces;

a base portion having proximal and distal end portions, said base portion being at least partially slidably disposed between said cam surfaces; and a pair of staple forming members pivotally secured to said base portion distal end, wherein distal movement of the base portion relative to said housing causes said staple forming members to pivot upon contact with a corresponding stationary cam surface of said housing.

7. The apparatus according to claim 6, wherein each staple forming member is secured to the distal end of said base portion by a single pivot pin.

8. The apparatus according to claim 7, wherein the distance between said pivot pins remains constant throughout the operation of the apparatus.

9. The apparatus according to claim 6, wherein each said staple forming member is spring biased in an open position.

10. The apparatus according to claim 6, wherein each said staple forming member has a curved exterior surface and the stationary cam surfaces of said housing contact said curved exterior surfaces to cause pivoting motion of said staple forming members.

11. The apparatus according to claim 6, wherein the housing has a substantially planar base plate and the stationary cam surfaces protrude from the planar base plate.

12. The apparatus according to claim 11, wherein said base portion is substantially restricted to longitudinal movement relative to said housing as the base portion moves between the stationary cam surfaces.

13. A surgical apparatus for applying a surgical staple which has a central portion and a pair of spaced apart legs extending from the central portion, said apparatus comprising:

a housing having proximal and distal end portions and a longitudinal axis;

a base portion having a longitudinal axis and proximal and distal end portions, said base portion being longitudinally slidable within said housing along said housing longitudinal axis; and a pair of staple forming members each pivotally secured by a single pivot pin to said base portion distal end, wherein longitudinal distal movement of the base portion relative to said housing longitudinal axis causes said staple forming members to pivot towards each other upon contact with a portion of said housing.

14. The apparatus according to claim 13, wherein the distance between said pivot pins remains constant throughout the operation of the apparatus.

15. The apparatus according to claim 13, wherein the housing has oppositally disposed raised cam surfaces which contact the staple forming members as the base portion slides longitudinally through the housing.

16. The apparatus according to claim 15, wherein the stationary cam surfaces substantially restrict said base portion to longitudinal movement within said housing.

17. The apparatus according to claim 13, wherein each said staple forming member has a curved exterior surface and the stationary cam surfaces of said housing contact said curved exterior surfaces to cause pivoting motion of said staple forming members.

18. The apparatus according to claim 13, wherein each said staple forming member is spring biased in an open position.

19. The apparatus according to claim 13, wherein the housing has a substantially planar base plate and oppositally disposed stationary cam surfaces protruding from the planar base plate and wherein the base portion is adapted to at least partially slide between the cam surfaces.

20. A surgical apparatus for applying a surgical staple which has a central portion and a pair of spaced apart legs extending from the central portion, said apparatus comprising:

a housing having proximal and distal end portions and oppositally disposed raised stationary cam surfaces;

a base portion having proximal and distal end portions, said base portion being at least partially slidably disposed between said cam surfaces; and a pair of staple forming members each pivotally secured by a single pivot pin to said base portion distal end, wherein distal movement of the base portion relative to said housing causes said staple forming members to pivot upon contact with a corresponding stationary cam surface of said housing and wherein the distance between said pivot pins remains constant throughout the operation of the apparatus.

* * * * *